US006413500B1

(12) United States Patent
Thorwaldson

(10) Patent No.: US 6,413,500 B1
(45) Date of Patent: Jul. 2, 2002

(54) METHOD AND APPARATUS FOR ORAL HYGIENE

(76) Inventor: W. S. Thorwaldson, 2332 S. Peck, #253, Whittier, CA (US) 90601-3253

( * ) Notice: Subject to any disclaimer, the term of this patent is extended or adjusted under 35 U.S.C. 154(b) by 0 days.

(21) Appl. No.: 09/573,115

(22) Filed: May 17, 2000

(51) Int. Cl.[7] .................. A61K 7/16; A61C 17/00; A61C 15/00
(52) U.S. Cl. .................. 424/49; 433/80; 433/215; 433/216; 433/217.1
(58) Field of Search ................ 424/49; 433/80, 433/216, 217.1

(56) References Cited

U.S. PATENT DOCUMENTS 5,104,315 A * 4/1992 McKinley .................... 433/80
5,129,824 A * 7/1992 Keller ......................... 433/215
5,855,870 A * 1/1999 Fischer ........................ 424/49

* cited by examiner

Primary Examiner—Frederick Krass
Assistant Examiner—Donna Jagoe
(74) Attorney, Agent, or Firm—Daniel L. Dawes; Myers, Dawes & Andras LLP

(57) ABSTRACT

A bacteria killing oral bactericide is applied to a user's teeth. All surfaces of the teeth are covered with the oral bactericide. The oral bactericide is left disposed on the teeth during the sleeping hours during which the oral bactericide both destroys harmful bacteria, plaque-building bacteria, and protects the teeth from any damage which may be caused by harmful bacteria. The oral bactericide is removed by brushing the teeth.

20 Claims, 1 Drawing Sheet

METHOD AND APPARATUS FOR ORAL HYGIENE

BACKGROUND OF THE INVENTION

1. Field of the Invention

The invention relates generally to oral hygiene and in particular to compositions, methods and devices for prevention of tooth decay and gum disease.

2. Description of Related Art

The human mouth is a sanctuary for harmful bacteria. Preventing the oral introduction is impractical. Though brushing several times throughout the day is recommended to remove food which provides a nutritional medium for bacteria, such diligence does little to protect the teeth when one is asleep and generally has little or no ability to kill bacteria which is harbored between the teeth and in the gums. The creation of plaque deposits results from the action of bacteria which in turn leads to gum disease.

In addition to toothpaste, various forms of bactericidal mouthwash are known in the art. The efficacy of such mouthwashes varies dramatically often with an inverse relationship between efficacy and acceptability to most users due to the taste and smell typical of strong bactericides. Such products are used by rinsing the mouth with the mouthwash during a day. It is known to rinse with mouthwash at night prior to retiring. However, such practice only destroys harmful bacteria at the time of use. Such protection typically lasts for only a few minutes. Thus, when a person is sleeping, the mouth, which is moist and warm, is left as an unprotected, ideal bacterial environment and is vulnerable to the damaging effects of harmful bacteria for several continuous hours. Moreover, the temporal duration of contact between the teeth and gums on one hand and the bactericidal mouthwash on the other is limited. To be effective, the bactericidal mouthwash must be very quick acting, which also tends to render it less acceptable for reasons of taste and smell. In addition, the more stringent the bactericidal mouthwash, the more likely that an adverse reaction will be experienced by a percentage of the users.

SUMMARY OF THE INVENTION

The invention is defined as a method for maintaining oral hygiene comprising the steps of providing an oral bactericide, disposing the oral bactericide on a user's teeth and/or gums, leaving the oral bactericide on the teeth for an extended length of time, and killing bacteria on and between the user's teeth and/or gums by means of the oral bactericide.

The step of providing an oral bactericide comprises the step of providing the oral bactericide as a paste, gel, liquid, or sprayed coating for application to the teeth and/or gums. The oral bactericide covers substantially all surfaces of the teeth. In general terms providing an oral bactericide comprises the step of applying a deformable solid carrier including the oral bactericide onto the teeth. In one embodiment the step of disposing the oral bactericide on a user's teeth comprises encapsulating the teeth with a guard, mold or retainer, which may be flexible or rigid and sometimes custom molded to the user's bite. In another embodiment the step of disposing the oral bactericide on a user's teeth comprises the step of disposing the oral bactericide onto a tool and using the tool to force the oral bactericide onto and between the teeth.

The oral bactericide is left in intimate contact with the teeth and/or gums during the sleeping hours, or typically for more than one hour. It is expressly within the scope of the invention that even shorter times may be employed than one hour where the bactericide is efficacious to kill the bacteria present during such shorter intervals. However, intimate contact with the bactericide is substantially longer than would ever likely occur with any known mouthwash. The killing of the bacteria inside the user's mouth by means of the oral bactericide maintains the oral bactericide in contact with the teeth and gums to inhibit the deposition of plaque.

The invention is also defined as an apparatus for maintaining oral hygiene comprising an oral bactericide, and a holder for the oral bactericide for disposing the oral bactericide on a user's teeth. The holder retains the oral bactericide on the teeth for an extended length of time in order to kill bacteria on and between the user's teeth and/or gums. Once again it is to be expressly understood that the holder for the oral bactericide may be a deformable solid moldable onto the user's teeth, a sprayable coating disposed onto the user's teeth, or a fixed and molded or flexible retainer disposable onto the user's teeth.

Although the method has been described in terms of steps for the purpose of grammatical fluency, it is to expressly understood that the methodology included within the definition of the claims and invention is not to be limited by the construction assumed for steps in 35 USC 112, but is to be understood as including the full range of meaning of the defining words the claims and their equivalents. The invention, now having been briefly summarized, may be better visualized by turning to the following drawings wherein like elements are referenced by like numerals.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

Figure 1:
FIG. 1 is a diagram illustrating one method of applying the oral bactericide according to the invention.

In FIG. 1, a bacteria killing oral bactericide 10 comprises an oral bactericide. Examples include any antibiotic agent now known or later devised, such as penicillin, amoxicillin, tetracycline, or cephalexin, which is carried in an inert dental, waterproof paste or gel. It is to be expressly understood that any oral bactericide may be employed, which is now known or later devised. The oral bactericide may be in the form of or carried in a paste or gel, which may be wet when first being applied by the user's finger or an oral applicator specifically designed for the purpose. For example, the gel or paste may be held in a squeezeable tube, similar to a tooth paste tube, and forced from the end of the tube through a soft rubber applicator or nozzle which serves to confine and direct the gel or paste onto the tooth surface. The oral bactericide may also comprise a liquid which would be sprayed onto the teeth, and then dried or set to form a coating. The carrier, whether it be a gel, paste, or spray coating, is sufficiently resistant to dissolution by saliva that it is retained on the teeth for the intended time period, typically a 6–8 hour sleeping period.

Preferably, all exposed surfaces of the teeth are encapsulated by the oral bactericide, including areas between two adjacent teeth, areas adjacent to the gums, and the lingual and bottom surfaces of the teeth. The common features of the various modes of application are that the oral bactericide is applied to all or almost all of the surfaces of the teeth and gums and it is applied in a form which is stable and remains in place for a number of hours, typically through a normal sleep period.

Figure 2:
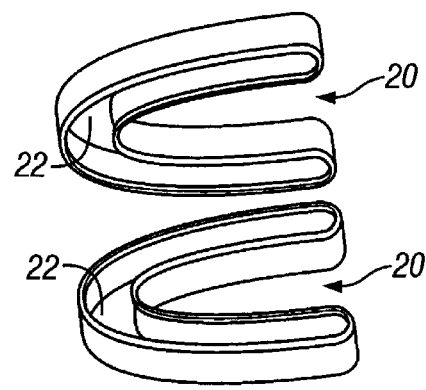
FIG. 2 is a perspective view of an upper and lower mold.

A variety of methods may be used to dispose the oral bactericide on a user's teeth. The user may simply apply the oral bactericide by using his or her fingers, as shown in FIG. 1. An instrument such as a Q-tip, or a soft plastic or rubber spatula may be used to spread the oral bactericide over the surfaces of the teeth. If desired, a mold or guard, such as the mold 20 shown in FIG. 2, is filled with the oral bactericide to hold it in place and to keep it firmly pressed against and between the teeth. Mold 20 is preferably made of a soft, deformable, plastic or rubber for the purposes of comfort and to minimize any possible irritation of the soft tissues in the mouth. Moreover, mold 20 doubly serves as a means to protect the teeth from users who grind their teeth unconsciously while asleep, which habitual grinding results in premature wear and tooth chipping. Since a mold 20 covers only the teeth on the upper or lower jaw, two molds are required to cover both the upper and lower rows of teeth. If molds are used, the oral bactericide may first be disposed in cavity 22 of the mold 20. Afterwards, the user may simply press the filled molds 20 against the teeth to form a tight fit with the oral bactericide inside the mold encapsulating the teeth. The oral bactericide may be carried in any type of carrier to facilitate its disposition in mold 20 and then its retention next to the teeth and gums. This may include an inert carrier which remains soft and pliable, or which sets to a certain resiliency to ensure its contact with the teeth for a number of hours.

Figure 3:
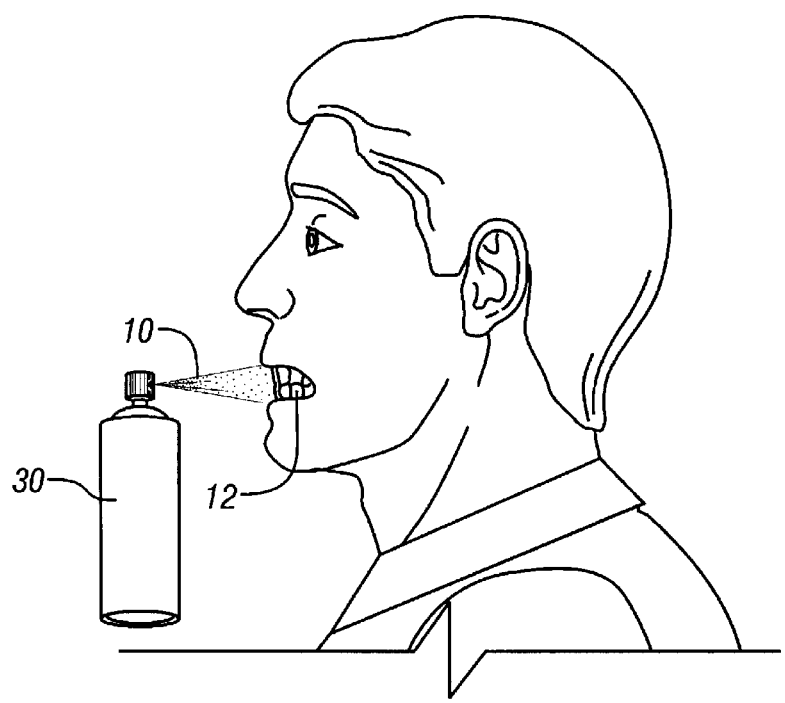
FIG. 3 is a diagram illustrating an alternate method of applying the oral bactericide.

If the oral bactericide is in the form of a liquid, as opposed to a gel or paste, the liquid oral bactericide 10 may be packaged in a spray bottle 30, as shown in FIG. 3. Alternatively, it may be painted on with a brush from a supply bottle. A user simply sprays the liquid 10 on the teeth 12. No mold would be necessary in such a case as the liquid disposed on the teeth would quickly dry out and become a thin coating. Alternatively, a quick air-setting carrier can be sprayed with the oral bactericide. Nonetheless, a mold or guard could be optionally worn to protect and prevent the coating from wearing out during its disposition on the teeth.

The oral bactericide may be applied at anytime. In the preferred embodiment, the oral bactericide is applied prior to sleeping. This time is preferable because the user will find it convenient to cover the teeth with the oral bactericide when he or she will not be speaking or eating. Thus, applying the oral bactericide prior to sleeping and leaving it in contact during the sleeping hours protects the user from damaging effects of harmful bacteria. Leaving it on the teeth during the sleeping hours also offers the advantage of the oral bactericide performing its work for several hours. Leaving the oral bactericide on the teeth during the sleeping hours is also convenient for the user in that he or she does not have to deal with it, or even be conscious of it, until morning when the oral bactericide is removed by brushing. In this aspect then it is preferable to have the oral bactericide disposed in a carrier which can readily be removed, i.e. either a carrier that retains a fair degree of self-affinity so that it can be peeled from the teeth in large sections, or which set to form an easily crumbled matrix that can be easily dislodged and swept from the teeth.

The oral bactericide acts as an offense and a defense against harmful bacteria in the mouth. Offensively, the oral bactericide destroys harmful bacteria. Defensively, the oral bactericide guards the teeth from bacteria and prevents build-up of plaque, which usually occurs as a result of an extended duration of food and saliva adhering to the surface of a tooth. Thus, when the oral bactericide is applied promptly after brushing, the oral bactericide both kills harmful bacteria and prevents such bacteria from invading and causing damage. Since the bacteria requires oxygen to survive, the bactericide and the inert carrier cuts off access to the needed oxygen, thereby suffocating the bacteria.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

What is claimed is:

1. A method for maintaining oral hygiene comprising:
   (a) administering an oral bactericide by disposing said oral bactericide on a user's teeth in a liquid, paste or gel carrier that forms a layer on said teeth, (b) leaving said oral bactericide on said teeth for a length of time of at least three minutes, thereby killing bacteria on and between said user's teeth by means of said oral bactericide, wherein said bactericide is disposed in said carrier, said carrier by itself is insoluble in saliva for at least six hours when not disturbed by mechanical action, wherein said carrier and bactericide further suffocate bacteria by cutting off access to oxygen, and (c) removing said carrier and bactericide by brushing said teeth by which the carrier is removed by peeling large sections of the carrier or by crumbling and sweeping the carrier from said teeth.

2. The method in claim 1 wherein administering an oral bactericide comprises providing said oral bactericide as a paste for application to said teeth.

3. The method in claim 1 wherein administering an oral bactericide comprises providing said oral bactericide as a gel for application to said teeth.

4. The method in claim 1 wherein administering an oral bactericide comprises providing said oral bactericide as a liquid for application to said teeth.

5. The method in claim 1 wherein disposing said oral bactericide on a user's teeth comprises spraying said oral bactericide on said teeth.

6. The method in claim 1 wherein disposing said oral bactericide in a carrier on a user's teeth comprises covering substantially all surfaces of said teeth.

7. The method in claim 1 wherein disposing said oral bactericide on a user's teeth further comprises encapsulating said teeth with a guard.

8. The method in claim 1 wherein leaving said oral bactericide on said teeth for said length of time comprises leaving said oral bactericide on said teeth during the sleeping hours.

9. The method in claim 1 wherein killing bacteria inside said user's mouth with said oral bactericide comprises maintaining said oral bactericide in contact with said teeth and gums to inhibit the deposition of plaque.

10. The method in claim 1 wherein disposing said oral bactericide on a user's teeth comprises applying a deformable solid carrier including said oral bactericide onto said teeth.

11. The method in claim 10 wherein applying said deformable solid carrier including said oral bactericide onto said teeth comprises applying a gel carrying said oral bactericide.

12. The method in claim 10 wherein applying said deformable solid carrier including said oral bactericide onto said teeth comprises applying a paste carrying said oral bactericide.

13. The method in claim 1 wherein disposing said oral bactericide on a user's teeth comprises disposing said oral bactericide into a retainer and then disposing said retainer onto said teeth.

14. The method in claim 1 wherein disposing said oral bactericide on a user's teeth comprises disposing said carrier including said oral bactericide onto a tool and using said tool to force said carrier including said oral bactericide onto and between said teeth.

15. An apparatus for maintaining oral hygiene comprising:

an oral bactericide; and a carrier carrying said oral bactericide for disposing said oral bactericide on a user's teeth, said carrier forming a single layer and retaining said oral bactericide on said teeth for a length of time of at least three minutes in order to kill bacteria on and between said user's teeth by means of said oral bactericide, wherein said carrier is a liquid, paste, or gel that forms a layer that is stable and remains on the teeth for at least six hours when not disturbed by mechanical action, wherein said carrier and bactericide further suffocate bacteria by cutting off oxygen, and said carrier by itself is insoluble in saliva for at least six hours, and wherein said carrier and oral bactericide are removed by brushing, by which brushing the carrier is removed by peeling large sections of the carrier or by crumbling and sweeping the carrier from said teeth.

16. The apparatus of claim 15 wherein said carrier for said oral bactericide is a deformable solid moldable onto said user's teeth.

17. The apparatus of claim 15 wherein said carrier for said oral bactericide is a sprayable coating onto said user's teeth.

18. The apparatus of claim 15 further comprising a holder for said carrier and oral bactericide, wherein said holder is a retainer disposable onto said user's teeth.

19. The apparatus of claim 15 further comprising a retainer disposable onto said user's teeth wherein said retainer is a fixed retainer.

20. The apparatus of claim 15 further comprising a retainer disposable onto said user's teeth wherein said retainer is a flexible retainer.

* * * * *